United States Patent [19]

He et al.

[11] Patent Number: 5,291,997

[45] Date of Patent: Mar. 8, 1994

[54] MEDICAL MAILER BOX ASSEMBLY

[76] Inventors: Yun-Ju He; Shang-Li Wu; Wei He, all of 5217 NW. 23rd Pl., Gainesville, Fla. 32606

[21] Appl. No.: 926,657

[22] Filed: Aug. 10, 1992

[51] Int. Cl.$^5$ .............................................. B65D 71/00
[52] U.S. Cl. ..................................... 206/370; 206/366; 206/571; 220/908; 229/921
[58] Field of Search .............................. 206/363–366, 206/570, 571, 523; 220/90 B, 375; 229/149, 151, 921

[56] References Cited

U.S. PATENT DOCUMENTS

| | | | |
|---|---|---|---|
| 2,727,675 | 12/1955 | Mairs et al. | 229/151 X |
| 3,409,204 | 11/1968 | Carle | 229/149 X |
| 3,593,909 | 7/1971 | Bergmann | 220/375 X |
| 4,121,755 | 10/1978 | Meseke et al. | |
| 4,240,547 | 12/1980 | Taylor. | |
| 4,250,998 | 2/1981 | Taylor | 206/570 |
| 4,452,358 | 6/1984 | Simpson | 206/366 |
| 4,520,926 | 6/1985 | Nelson | 206/366 |
| 4,600,112 | 7/1986 | Shillington et al. | 206/366 X |
| 4,863,052 | 9/1989 | Lambert. | |
| 4,886,164 | 12/1987 | Stein et al. | |
| 4,969,554 | 11/1990 | Sawaya. | |
| 4,972,950 | 11/1990 | Shillington | 206/366 |
| 5,038,929 | 8/1991 | Kubofcik | 206/366 X |
| 5,039,004 | 8/1991 | Simpson | 206/571 X |
| 5,096,114 | 3/1992 | Higgenbotham. | |
| 5,172,808 | 12/1992 | Bruno | 206/366 |
| 5,184,721 | 2/1993 | Wengyn et al. | 206/366 |

FOREIGN PATENT DOCUMENTS

| | | | |
|---|---|---|---|
| 869863 | 5/1971 | Canada | 206/523 |
| 9008713 | 8/1990 | PCT Int'l Appl. | 206/366 |
| 9117099 | 11/1991 | PCT Int'l Appl. | 206/366 |

Primary Examiner—Bryon P. Gehman
Attorney, Agent, or Firm—Michael K. Gray

[57] ABSTRACT

An assembly for housing medical supplies and for storing and mailing medical waste contained therein having an exterior box made of corrugated paper into which a plastic removable medical waste container can be inserted into and secured in a container bay provided by styrofoam insulation which contacts the interior sidewalls of the exterior box. The styrofoam insulation is provided with a plurality of apertures to accommodate syringes. Upon using the syringes, a user can place the syringe through an aperture in the medical waste container. Upon using all of the syringes originally provided with the assembly and placing them inside the medical waste container, the aperture provided in the medical waste container is latched closed and the medical waste container is placed inside the exterior box in the bay provided by the styrofoam insulation. The exterior box is then closed by closing the foldable top of the exterior box and inserting flaps attached to the foldable top to insertion holes provided at the front side of the exterior box. A pair of folded and bent appendages centrally located on the foldable top are inserted into accommodating holes located in the front of the exterior box so as to permanently lock the exterior box such that it cannot be opened without destroying the lock system. The assembly is then mailed to an appropriate disposal sight for incineration.

12 Claims, 4 Drawing Sheets

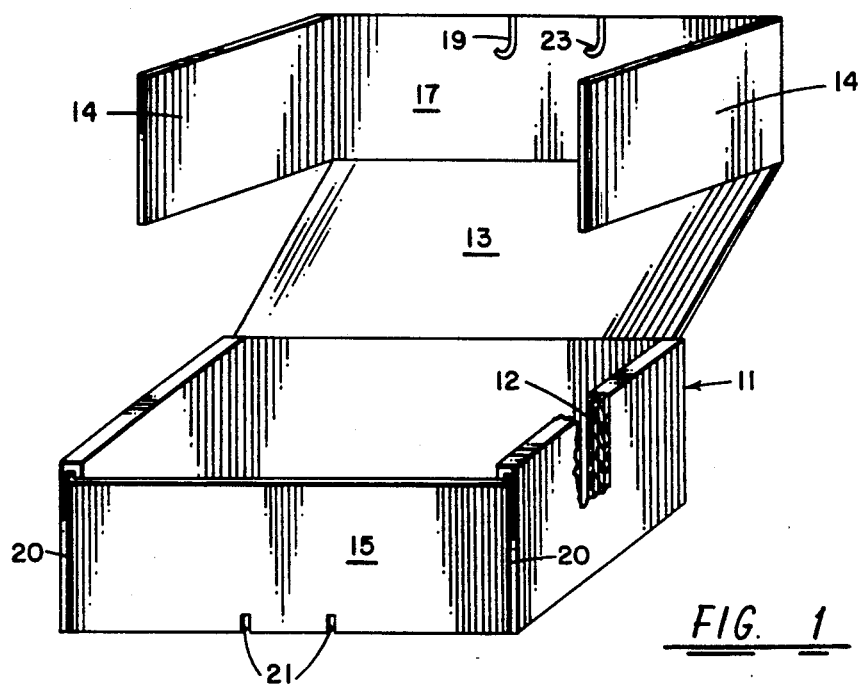
FIG. 1
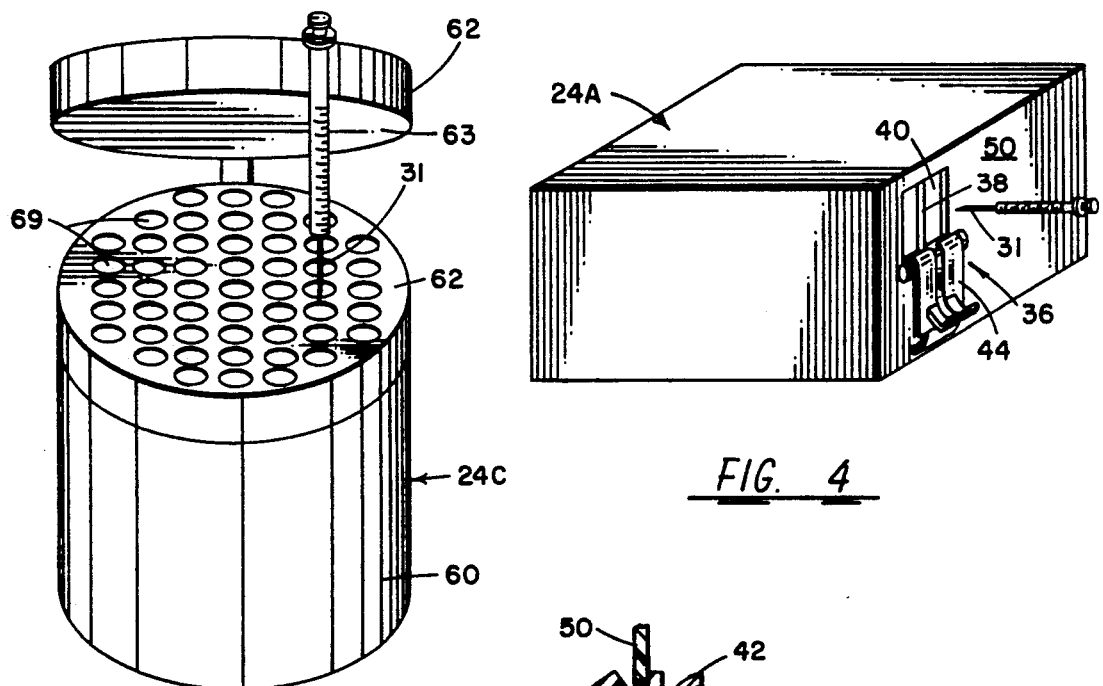
FIG. 7
FIG. 4
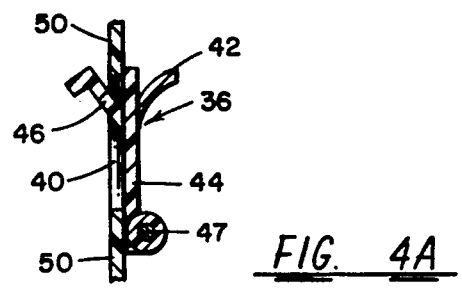
FIG. 4A

MEDICAL MAILER BOX ASSEMBLY

BACKGROUND OF THE INVENTION

1. Field of the Invention

The present invention relates to devices for the storage and disposal of medical waste. More particularly, the present invention relates to a medical mailer box assembly which when first mailed to a patient contains appropriate medical supplies and instruments which after use can be disposed of in a medical waste container provided with the mailer box assembly. The medical waste container is then sealed and replaced back inside of an exterior box of the medical mailer assembly and mailed to an appropriate location for incineration.

2. Discussion of the Background

The prior art demonstrates a number of devices which are for the purpose of disposing of medical waste and materials. In recent years, with the heightened awareness of such diseases as hepatitis and AIDS, the safe containment and disposal of medical waste and instruments has become an increasing concern.

U.S. Pat. No. 4,121,755 to Meseke et al discloses a disposable container made of cardboard or a synthetic material for disposing of medical waste. U.S. Pat. No. 4,240,567 to Taylor discloses a specimen mailer comprised of two polystyrene foam parts which are surrounded by a mailing envelope. U.S. Pat. No. 4,863,052 to Lambert. U.S. Pat. No. 4,886,164 to Stein et al. and U.S. Pat. No. 5,096,114 to Higgenbotham, all reveal disposable containers for medical waste. U.S. Pat. No. 4,969,554 to Sawaya reveals a polypropylene container for disposing of syringes.

In certain types of diseases, such as diabetes, patients typically receive and administer medication on their own. For example, a typical diabetes patients will give his or herself daily shots of insulin by means of a hypodermic needle. Upon using the hypodermic needle, a need arises to dispose of it in a proper and safe manner.

Thus, a need is seen for a medical mailer box assembly which can provide a patient with needed medical instruments and materials and which is provided with means for disposing of the instruments and materials in such a manner that the box assembly can be repackaged, with the used medical instruments and materials safely secured therein, and mailed to an appropriate location for incineration.

SUMMARY OF THE INVENTION

Accordingly, one object of the present invention is to provide a novel medical mailer box assembly which can be used to provide medical materials and instruments and which can later be used to dispose of the materials and instruments.

Yet another object of the present invention is to provide a box assembly which includes a medical waste container which is durable and protective, but which can be easily incinerated.

Still another object of the present invention is to provide a box assembly which will reduce medical costs and increase safety.

These and other valuable objects and advantages of the present invention are provided by an assembly for housing medical supplies and for storing and mailing medical waste contained therein. A mailer box is used to house a medical waste container which is provided with an aperture for the insertion of medical, waste, and used supplies. Insulation and securing means (medical supply housing) contacts the interior walls and bottom of the mailer box with the insulation and securing means being provided with a bay or accommodating means for accommodating the medical waste container inside of the mailer box. Means are provided for preventing the medical waste contained inside the medical waste container from escaping the confines of the container. The insulation and securing means is further provided with means for accommodating medical instruments or supplies. Thus, the mailer box assembly of the present invention is used to supply new and dispose of used medical instruments and materials.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a perspective illustration of the exterior box of the box assembly of the present invention;

FIG. 4 is a perspective illustration of one embodiment of the medical waste container according to the present invention;

FIG. 4A is a side-view cross-sectional illustration of the latch means of the medical waste container of FIG. 4;

FIG. 7 is a perspective illustration of still another embodiment of the medical waste container according to the present invention.

When referring to the drawings it is understood that like reference numerals identify similar or corresponding parts throughout the respective views and figures.

THE DETAILED DESCRIPTION OF THE INVENTION

Figure 2:
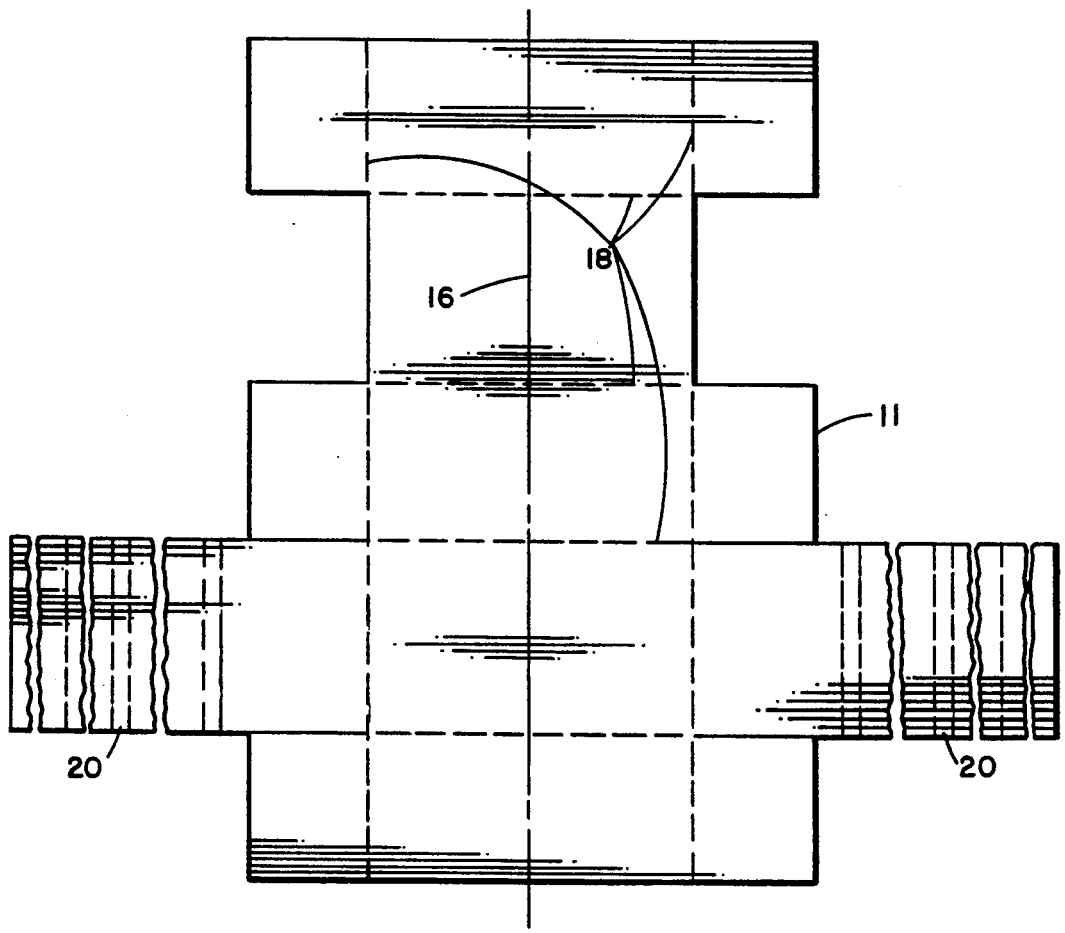
FIG. 2 is top view illustration of the exterior box of FIG. 1 in an unfolded state.

In FIG. 1 an exterior mailer box 11 is made of corrugated paper or cardboard having four layers as is indicated in the cutaway region indicated by numeral 12. A foldable top 13 of mailer box 11 is connected to flaps 14 which are positioned at opposite ends of front overlap region 17. The flaps are insertable into the insertion holes 20 provided at the opposite ends of the front side 15 of box 11.

Still with reference to FIG. 1, front overlap region 17 is further provided with two corrugated paper hook appendages 19 each having a fold region 23 which is bent in such a manner that the appendages 19 can be inserted into holes 21 provided at the bottom of the front side 15 of the mailer box 11. The holes 21 are sized to allow entry of the hooked appendages 19, with the appendages 19 being bent in such a manner that the respective fold regions 23 are easily inserted into the respective holes 21. However, once inserted into the holes 21, the elasticity and shape of the fold regions 23 prevent the opening of the mailer box 21. Appendages 19 and holes 21 comprise a corrugated die cut lock tab which is used when it is desirable to seal the box 11 for a final time (such as when the box 11 and its contents are to be mailed for a final time).

In FIG. 2, box 11 is depicted in a flat, unfolded and unassembled state. The center line of the box 11 is indicated at numeral 16 Folding lines are indicated by numeral 18. The box 11 as shown in FIG. 2 can be folded to achieve the assembled box of FIG. 1 having a bottom, sides and top.

Figure 3:
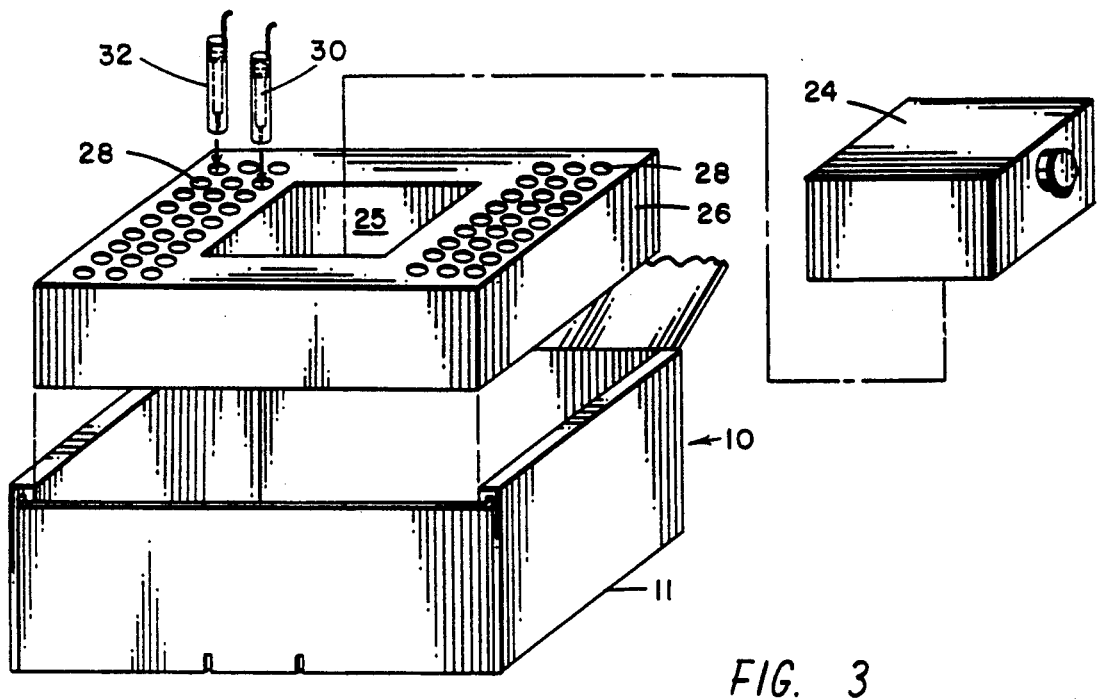
FIG. 3 is an exploded view of the box assembly of the present invention according to one embodiment thereof.

In FIG. 3 the box assembly, 10, includes the exterior box 11 into which is placed a medical supply housing 26 which is provided with a container bay 25 which is formed to accommodate and which surrounds a medical waste container 24. The medical waste container 24 is intended for the containment of biohazardous materials such as used syringes, hypodermic needles, and alcohol swabs. The medical waste container 24 is not intended for the containment of liquid waste. Medical supply housing 26 is made of styrofoam or other appropriate material and contacts the interior sidewalls of exterior box 11. A plurality of storage spaces (apertures) 28 are provided in the medical supply housing 26 for storing unused medical instruments and the like (e.g., syringes and hypodermic needles 30 packaged in a plastic container 32).

Figure 3A:
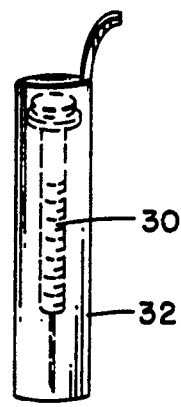
FIG. 3A is a perspective illustration of a packaged hypodermic needle and syringe.

FIG. 3A illustrates a syringe and hypodermic needle 30 which are packaged in cellophane container 32. Syringes and hypodermic needles 30 such as those illustrated in FIG. 3A can be packaged and housed in apertures 28 of the medical supply housing 26 and mailed to a patient.

In FIG. 4 medical waste container 24A is provided with a latching means 36 for latching and closing the aperture 40 which provides an entrance into the interior of medical waste container 24A. For example, the used hypodermic needle and syringe 31 can easily be inserted through the aperture 40 which is positioned on side 50 of container 24A. The container 24A is preferably made of blow molded plastic; however, a durable, lightweight and easily incinerated material may be used as a substitute. The latching means 36 includes a support pin 38 which is positioned across aperture 40, with support pin 38 being connected at both of its ends to side 50 of container 24A. Since it is desirable that the latching means 36 be made of heavier plastic than side 50, the support pin 38 provides greater support and stability for the operation of the latching means 36.

The latching means 36 will be better understood with reference to FIG. 4A. A latch 44 is pivotable about rotable pin 47 which is supported at its opposite ends by a pair of flanges 45 which are molded to the side 50. Alternatively, the latch 44 could be provided with cylindrical side projections which are accommodated by and rotatable in form-fitted flanges. The latch 44 is provided with an appendage 46 which allows the latching means 36 to close in a first position (as shown in FIG. 4A) and an appendage 42, which when pushed down and forward, permanently closes the aperture 40 and locks and secures the contents of the medical waste container 24A. In the permanently closed position, the top of latch 44 is popped through the aperture 40 so as to be on the interior side of side 50. The latch 44 has an interior ridge to accommodate the support pin 38 and the appendage 46 is bifurcated to allow the latching means to close while accommodating the support pin 38.

Figure 5:
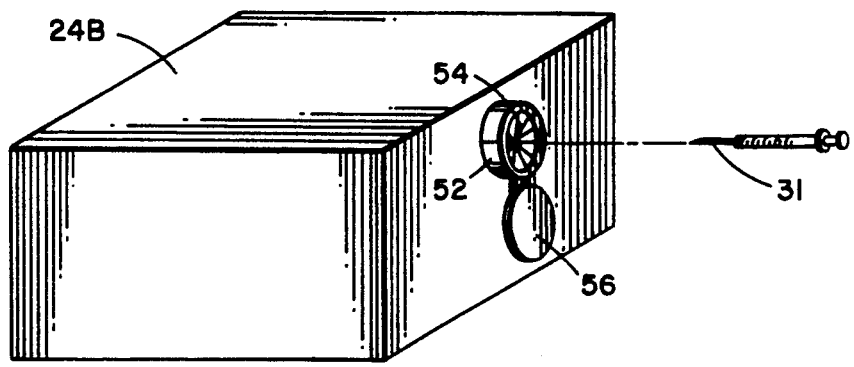
FIG. 5 is a perspective illustration of a second embodiment of the medical waste container according to the present invention having a plastic filter with a one-way insertion means.
Figure 5A:
FIG. 5A is a front view illustration of the one-way insertion means of FIG. 5.

With reference to FIG. 5, medical waste container 24B is another embodiment of waste containers 24 according to the present invention. Container 24B has a plastic filter 52 through which materials such as used hypodermic needle and syringe 31 can be inserted into the interior of container 24B. Plastic filter 52 is provided with triangular plastic strips which are slanted inward to form a one-way insertion means 54. A plastic cap 56 is provided to close the entrance of the filter. FIG. 5A provides a better appreciation of the oneway insertion means 54 of the plastic filter 52 by illustrating the triangular and inwardly slanted nature of the plastic strips which form the one-way insertion means 54.

Figure 6:
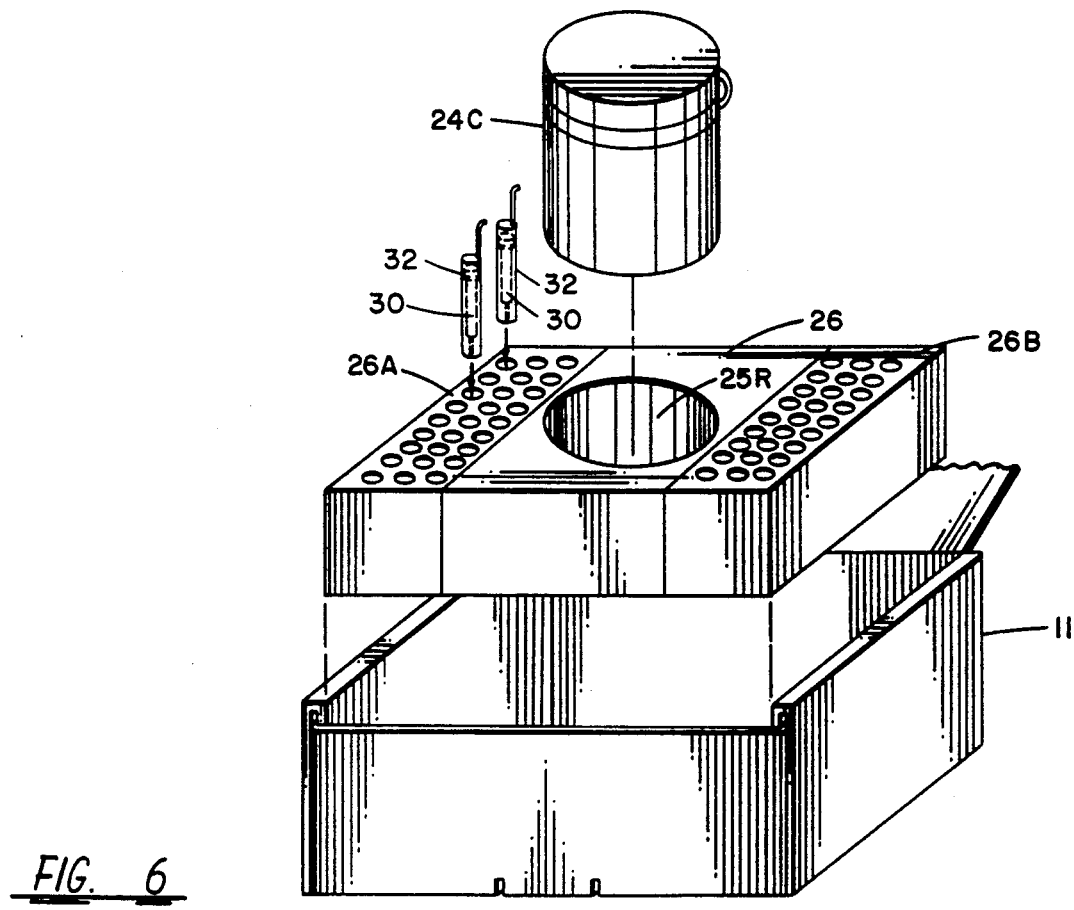
FIG. 6 is an exploded view of another embodiment of the box assembly of the present invention.

In FIG. 6 the medical supply housing 26 is divided into contiguous segments (such as segments 26A and 26B). Segments 26A and 26B are equipped with container apertures 28 for accommodating syringes or other medical instruments. A container bay 25R is shaped to accommodate medical waste container 24C. FIG. 6 further serves to demonstrate the detachable nature of the medical waste container 24, medical supply housing 26, and mailer box 11.

In FIG. 7, jar-shaped medical waste container 24C is provided with a plastic cylindrical body 60 which houses a foam plastic container 62 having a plurality of apertures 69 for accommodating used syringes such as syringe 31. A plastic top 62 is provided with a soft foam plastic interior layer 63 for covering and closing the waste container 24C.

Figure 8:
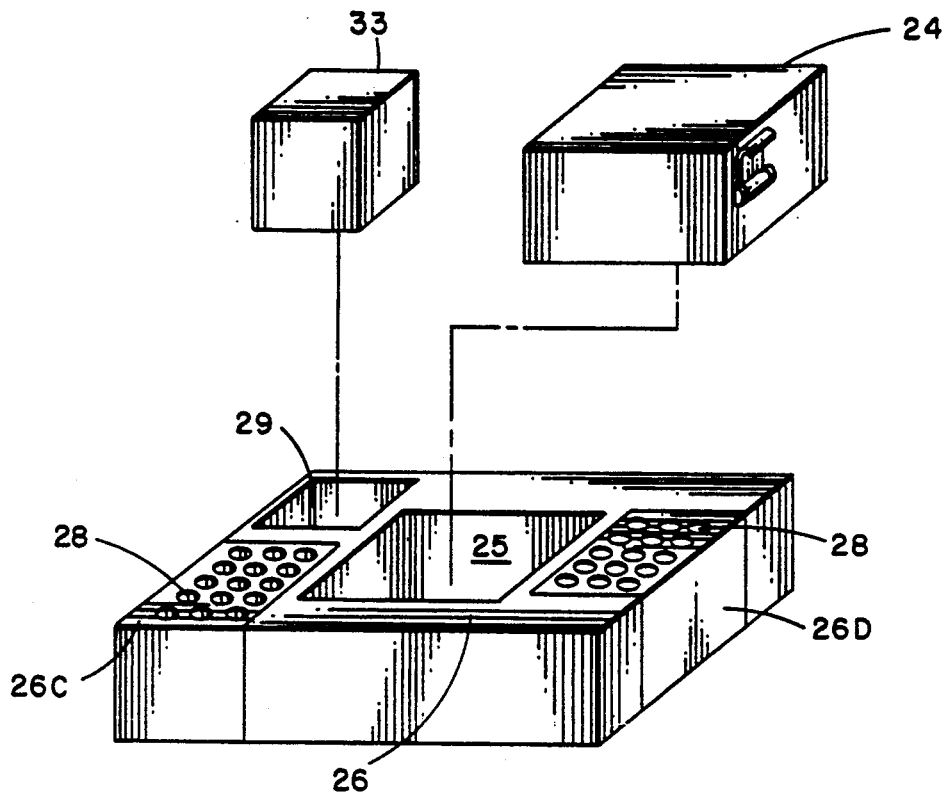
FIG. 8 is a partial exploded perspective illustration of the insulation and securing means and medical waste container according to yet another embodiment of the present invention.

In FIG. 8, medical supply housing 26 is provided with container bay 25R for accommodating medical waste container 24C and is further provided with a bay 29 to accommodate a medical supply box 33 which could, for example, be filled with alcohol swabs. Insulation and securing means 26 is provided with contiguous segments 26C and 26D which are provided with apertures 28 for accommodating packaged and unused syringes.

In use the box assembly 10 of the present invention could be utilized such that patients could be sent medical supplies which are packaged and housed in the medical supply housing 26. For example, hypodermic needles and syringes can be provided in the medical supply housing 26. After using a syringe and hypodermic needle, the patient would place the syringe and hypodermic needle inside of the medical waste container 24 by inserting the used syringe and needle through the aperture leading to the interior of the medical waste container.

Thus, the likelihood of using a contaminated needle is reduced for the patient and the probability of others coming in contact with a contaminated needle is reduced as well. After all of the hypodermic needles are used and placed inside a container 24, the container 24 is placed into the container bay (25, 25R) provided by the insulation and securing means 26 inside the box 11 which is closed (permanently closed by utilizing the appendages 19 and holes 21 of FIG. 1) and mailed to an incineration location.

It is surmised that initially a patient would be given two box assemblies 10 filled with medical materials. After the materials in one box have been used, the patient would mail the used contents housed in the box assembly 10 to a medical incineration facility. The outside of the box could identify a patient by a code number so upon the medical incineration facility receiving the box assembly 10 for incineration, it would be known that the patient should be sent a new box full of unused medical materials and supplies. The incineration facility could be computer linked to a distribution center so that a patient would always have an adequate supply of needed medical materials. The present invention is very useful for diabetes patients and other types of patients who must self-administer medication.

Numerous changes and modifications of the present invention are possible in light of the above teachings. Therefore, it is understood that the invention may be practiced otherwise than as specifically described herein and still be within the scope of the appended claims.

What is claimed is:

1. An assembly for housing medical supplies which are packaged and unused and for storing and then mailing the medical supplies after the medical supplies have been unpackaged and used, said assembly comprising:
   a medical waste container having an aperture for allowing used medical supplies to be placed therein for storage;
   a medical supply housing having a bay into which said medical waste container is inserted, said medical supply housing being provided with a plurality of apertures;
   a plurality of packaged hypodermic needles and syringes inserted into the plurality of apertures of said medical supply housing, respectively; and
   a mailer box which contacts said medical supply housing and into which said medical waste container and said medical supply housing are inserted.

2. An assembly according to claim 1, wherein: said medical waste container is easily detachable from said medical supply housing.

3. An assembly according to claim 2, wherein said medical supply housing is easily detachable from said mailer box.

4. An assembly according to claim 1, wherein: said medical waste container is provided with means for closing the aperture.

5. An assembly according to claim 4, wherein said means for closing the aperture is a latch having a first appendage and a second appendage.

6. An assembly according to claim 1, wherein said medical supply housing surrounds said medical waste container.

7. An assembly according to claim 1 wherein said mailer box has a foldable top for closing and opening purposes.

8. An assembly according to claim 1, wherein said mailer box has a corrugated die-cut lock tab comprising:
   a pair of appendages having folded regions connected to a front overlap region of said mailer box for insertion into corresponding holes located in a front side of said mailer box.

9. An assembly according to claim 1, wherein said medical waste container is comprised of a one-way filter positioned over the aperture for allowing medical waste to be inserted into said medical waste container while preventing medical waste from leaving said medical waste container, said one-way filter being comprised of plastic strips which slant toward the interior of said medical waste container and obstruct the aperture of said medical waste container.

10. An assembly according to claim 1, wherein said medical waste container is made of molded plastic.

11. An assembly according to claim 1, wherein said mailer box is made of corrugated paper.

12. An assembly according to claim 1, wherein said medical waste container is a jar having a plurality of apertures, said jar having a removable cap.

* * * * *